United States Patent [19]
Godec et al.

[11] Patent Number: 5,902,751
[45] Date of Patent: May 11, 1999

[54] METHOD AND APPARATUS FOR THE MEASUREMENT OF DISSOLVED CARBON

[75] Inventors: Richard Godec, Longmont; Kevin O'Neill; Richard Hutte, both of Boulder, all of Colo.

[73] Assignee: Sievers Instruments, Inc., Boulder, Colo.

[21] Appl. No.: 08/798,212

[22] Filed: Feb. 10, 1997

Related U.S. Application Data

[60] Division of application No. 08/501,597, Jul. 12, 1995, which is a continuation-in-part of application No. 07/869,308, Apr. 16, 1992, Pat. No. 5,443,991, which is a division of application No. 07/487,720, Mar. 2, 1990, Pat. No. 5,132,094.

[51] Int. Cl.$^6$ .......................... G01N 33/18; G01N 27/00
[52] U.S. Cl. .......................... 436/146; 436/145; 436/55; 422/78; 422/79; 422/80; 422/82.02; 422/82.03
[58] Field of Search .................. 422/78, 79, 80, 422/81, 82.01, 82.02, 82.03; 436/62, 55, 145–149, 150, 174, 180

[56] References Cited

U.S. PATENT DOCUMENTS

| | | | |
|---|---|---|---|
| 3,224,837 | 12/1965 | Moyat | 23/230 |
| 3,958,941 | 5/1976 | Regan | 23/253 |
| 4,209,299 | 6/1980 | Carlson | 23/230 R |
| 4,277,438 | 7/1981 | Ejzak | 422/80 |
| 4,288,229 | 9/1981 | Mar | 23/230 PC |
| 4,293,522 | 10/1981 | Winkler | 422/80 |
| 4,504,373 | 3/1985 | Mani et al. | 204/180 |
| 4,529,495 | 7/1985 | Mansoner | 204/411 |
| 4,619,902 | 10/1986 | Bernard | 436/145 |
| 4,626,413 | 12/1986 | Blades et al. | 422/78 |
| 4,666,860 | 5/1987 | Blades et al. | 436/146 |
| 4,749,657 | 6/1988 | Takahashi et al. | 436/146 |
| 4,775,634 | 10/1988 | Sienkiewicz | 436/14 |
| 5,047,212 | 9/1991 | Blades et al. | 422/84.02 |
| 5,141,717 | 8/1992 | McRae | 422/82.01 |
| 5,312,756 | 5/1994 | Jolly | 436/8 |

*Primary Examiner*—Long V. Le
*Attorney, Agent, or Firm*—Lappin & Kusmer LLP

[57] ABSTRACT

Apparatus and methods for the measurement of total organic carbon, total inorganic carbon and total carbon of water are described. The ample is acidified and split into an inorganic carbon stream and a total carbon stream. The inorganic carbon in the inorganic stream is oxidized and both the organic and inorganic carbon in the total carbon stream is oxidized. The resulting carbon dioxide is measured in each stream using carbon dioxide sensors employing a gas permeable membrane dividing deionized water from the oxidized sample water and a pair of micro-conductivity and temperature sensors.

45 Claims, 3 Drawing Sheets

METHOD AND APPARATUS FOR THE MEASUREMENT OF DISSOLVED CARBON

This application is a divisional of application No. 08/501,597, filed Jul. 12, 1995, which is a continuation-in-part of application No. 07/869,308 filed Apr. 16, 1992, now U.S. Pat. No. 5,443,991, which is a division of application No. 07/487,720 filed Mar. 2, 1990, now U.S. Pat. No. 5,132,094, the contents of which are hereby incorporated by reference.

FIELD OF THE INVENTION

The present invention relates to an improved method and apparatus for the determination of the total concentration of organic and/or inorganic carbon compounds in aqueous process streams and in bulk solutions. Particularly, the method of the present invention in a preferred embodiment includes the acidification of an aqueous sample stream, the oxidation of the sample stream, and the sensitive and selective detection of carbon dioxide utilizing a gas permeable membrane and conductometric detection to determine the levels of organic carbon, inorganic carbon and/or total carbon.

BACKGROUND OF THE INVENTION

The measurement of the total organic carbon (TOC) concentration and total carbon (organic plus inorganic) concentration in water has become a standard method for accessing the level of contamination of organic compounds in potable waters, industrial process waters, and municipal and industrial waste waters. In addition to widespread terrestrial applications, the measurement of TOC is one of the primary means of determining the purity of potable and process waters for manned space based systems including the space shuttle, the proposed space station and for future manned explorations of the moon and planets.

The United States Environmental Protection Agency recently promulgated new rules aimed at reducing the levels of disinfectant by-products in drinking water. Formed from the reaction of chlorine and other disinfectants with naturally occurring organic matter, disinfectant by-products are potentially hazardous compounds including trihalomethanes ($CHCl_3$, $CHBrCl_2$, etc.), haloacetic acids, and other halogenated species. The new rules also include monitoring the levels of natural organic material in raw water, during the treatment process and in the finished water by measurement of total organic carbon concentration.

A variety of prior art approaches for measuring the total organic carbon content of water have been proposed. For example, See U.S. Pat. Nos. 3,958,941 of Regan; 3,224,837 of Moyat; 4,293,522 of Winkler; 4,277,438 of Ejzak; 4,626,413 and 4,666,860 of Blades et al.; and 4,619,902 of Bernard.

Representative of the devices described in these references are the methods disclosed in U.S. Pat. No. 3,958,941 of Regan. In Regan an aqueous sample is introduced into a circulating water stream that flows through a reaction chamber where the sample is mixed with air and exposed to ultraviolet (U.V.) radiation to promote the oxidation of organic compounds to form carbon dioxide. The carbon dioxide formed in the reaction chamber is then removed from solution by an air stripping system and introduced into a second chamber containing water that has been purified to remove ionic compounds. The conductivity of the water in the second chamber is measured, and any increase in conductivity is related to the concentration of carbon dioxide formed in the first reactor. The conduction measurement can be used, therefore, to determine the concentration of organic compounds in the original sample.

The Regan device is slow, cannot be used for the continuous monitoring of TOC concentration in aqueous streams, cannot be scaled down without increasing interference from $NO_2$, $CO_2$, and $H_2S$ to unacceptable levels, and is generally unsatisfactory. In addition, Regan does not disclose that an aqueous solution of acid must be added to the sample stream to reduce the pH to a value of less than about 4 to ensure a reasonable removal rate of carbon dioxide using the air stripping system described. The oxidation method disclosed by Regan is unsatisfactory for the measurement of refractory compounds, particularly urea. In Regan, an aqueous sample of 20 to 100 mL containing 0.5 mg/L organic carbon is required to generate sufficient carbon dioxide for accurate detection, thus limiting the utility of the device for the measurement of sub-part per million levels of TOC in smaller sample sizes. Finally, in practice, the Regan system requires frequent recalibration—typically once per day—due to variations in background conductivity. Also, the concentration of total organic carbon in the calibration standard must be approximately equal to the concentration of organic carbon in the sample. Because of this, recalibration is required when analyzing aqueous samples containing higher or lower levels of organic carbon when compared with the calibration standard.

The use of aqueous solutions of persulfate salts for the oxidation of organic compounds is widely known. Smit and Hoogland (16 Electrochima Acta, 1–18 (1971)) demonstrate that persulfate ions and other oxidizing agents can be electrochemically generated. In U.S. Pat. No. 4,504,373 of Mani et al., a method for the electrochemical generation of acid and base from aqueous salt solutions is disclosed.

An improved method and apparatus for the measurement of organic content of aqueous samples is disclosed in U.S. Pat. No. 4,277,438 of Ejzak. Ejzak describes a multistage reactor design which provides for the addition of oxygen and a chemical oxidizing agent, preferably sodium persulfate, to the aqueous sample stream prior to oxidation of the stream using ultraviolet radiation in a series of reactors. Ejzak also describes the use of an inorganic carbon stripping process—before oxidation of the organic carbon—that includes the addition of phosphoric acid to the sample stream. After oxidation, the sample stream is passed into a gas-liquid separator where the added oxygen acts as a carrier gas to strip carbon dioxide and other gases from the aqueous solution. In the preferred embodiment, the gas stream is then passed through an acid mist eliminator, a coalescer and salt collector, and through a particle filter prior to passage into an infrared (IR) detector for the measurement of the concentration of carbon dioxide in the gas stream.

The methods and apparatus disclosed by Ejzak provide improvements over the teachings of Regan; however, the Ejzak device requires extensive manual operation and is also generally unsatisfactory. The Ejzak device requires three external chemical reagents; oxygen gas, aqueous phosphoric acid and an aqueous solution of sodium persulfate. Both the phosphoric acid and persulfate solutions must be prepared at frequent intervals by the operator due to the relatively high rate of consumption. The Ejzak device requires dilution of the sample if the solution contains high concentrations of salts in order to ensure complete oxidation of the sample and to eliminate fouling of the particle filter located prior to the IR carbon dioxide detector. As with Regan, relatively large sample sizes are required—typically 20 mL of sample for accurate measurement at 0.5 mg/L total organic carbon—and the carbon dioxide formed in the oxidation chamber is removed using a gravity dependent technique that cannot be easily used in space-based operations.

Another improved method and apparatus for the measurement of total organic carbon in water is disclosed in U.S. Pat. No. 4,293,522 of Winkler. In Winkler, an oxidizing agent, molecular oxygen, is generated in-situ by the electrolysis of water. Organic compounds are subsequently oxidized to form carbon dioxide by the combination of U.V. radiation and the in-situ generated oxygen. The irradiation and electrolysis processes are both accomplished in a single oxidation chamber. Winkler does not teach that the aqueous sample stream be acidified to assist in the removal of carbon dioxide from solution, and in fact teaches against the use of acid. Therefore, this method and apparatus cannot be used for the measurement of organic compounds in basic aqueous samples. The oxidation chamber of Winkler uses a solid electrolyte to separate the two electrodes employed for the electrolysis of water. The solid electrolyte described by Winkler is composed of an organic polymer which, under exposure to oxygen, ozone and U.V. radiation, will undergo oxidation to form carbon dioxide, therefore resulting in unacceptable background levels of organic compounds in the sample stream, particularly at low organic compound concentrations.

Winkler also describes a conductometric carbon dioxide detection system wherein the sample stream exiting the oxidizing chamber is held in an equilibrating relationship to a stream of deionized water. The two flowing streams are separated by a gas permeable membrane that allows the concentration of carbon dioxide to equilibrate between the streams. The concentration of the carbon dioxide is thereby determined by measuring the conductance of the deionized water stream. However, the use of two flowing streams introduces operating parameters into the detection process that require frequent calibration adjustments.

Another example of the prior art is disclosed in U.S. Pat. No. 4,619,902 of Bernard, which teaches the oxidation of organic compounds to form carbon dioxide using persulfate oxidation at elevated temperatures—typically 20 to 100° C.—in the presence of a platinum metal catalyst. Bernard recognizes that the materials used in the construction of instrumentation for the determination of total organic carbon in water can contribute organic compounds to the sample during the measurement process, and teaches that inert materials such as PTFE must be used to reduce this background from the measurement. As with the previously mentioned disclosures, a gas stripping technique is employed to collect the formed carbon dioxide, and measurement is made using IR spectrometry. Bernard also recognizes that aqueous solutions of sodium persulfate are not stable due to auto-degradation of the reagent.

An improved system for the measurement of organic compounds in deionized water is disclosed in U.S. Pat. No. 4,626,413 of Blades and Godec. The apparatus described by Blades and Godec is based on direct U.V. oxidation of organic compounds to form carbon dioxide which is measured by using conductometric detection. In the apparatus described in Blades and Godec, the oxidation of some organic compounds form strong acids such as HCl, $H_2SO_4$ and $HNO_3$ which interfere with the conductometric method. The Blades device is also limited to the measurement of total organic compounds in deionized water and cannot be used for samples containing ionic compounds other than bicarbonate ion.

In U.S. Pat. No. 4,209,299 of Carlson, it is disclosed that the concentration of volatile materials in a liquid can be quantitively determined by transferring the desired material through a gas permeable membrane into a liquid of known conductivity, such as deionized water. The Carlson device is demonstrated for the measurement of a number of volatile organic and inorganic compounds, but Carlson does not suggest the combination of this process in conjunction with a carbon dioxide producing reactor.

In electrochemical reactions in aqueous solutions, a common reduction product is hydrogen gas. Because of its flammability, the hydrogen presents a potential hazard in devices using electrochemical techniques. The interaction of hydrogen gas in aqueous solutions and palladium metal is well known (e.g., F. A. Lewis, "The Palladium Hydrogen System," Academic Press, 1967, London, incorporated herein by this reference) and the use of palladium offers a potential solution to the generation of hydrogen in electrochemical reactions by selective removal and disposal of the hydrogen.

An improved carbon analyzer is disclosed in U.S. Pat. No. 5,132,094 by Godec et al., of which the present is a continuation-in-part. Originally developed for NASA, the Godec device uses UV/persulfate oxidation and a new $CO_2$ detection technique and membrane-based conductivity. A gas-permeable membrane is used to separate the acidified sample stream (pH<2) from a thin layer of deionized water. A solenoid valve is opened to allow fresh DI water to flow into the membrane module and the solenoid valve is closed. Carbon dioxide formed from the oxidation of organic compounds will diffuse across the membrane into the deionized water, where at a pH of about 7 a portion of the $CO_2$ will ionize to produce H+ and $HCO_3$-ions. After an equilibration period, the solenoid valve is opened to flush the ions into a conductivity and temperature measurement cell, and the concentration of $CO_2$ in the deionized water is determined from the conductivity.

Membrane-based conductivity detection of $CO_2$ offers several advantages. Calibration is extremely stable, and the calibration can be easily performed by the analyst. No purge gases are required. The technique is highly selective for $CO_2$ and is extremely sensitive, permitting detection of TOC down to sub-parts per billion levels. It also has a wide dynamic range, permitting measurement up to 50 ppm TOC.

In operation the sample is drawn into the analyzer by means of a peristaltic pump, and two reagents are added via syringe pumps. Acid (6 M $H_3PO_4$) is added to reduce the pH of the sample stream and persulfate (15% $(NH_4)_2S_2O_8$) is added for the oxidation of organic compounds. The sample stream is split for measurement of inorganic carbon (IC) concentration (IC=[$HCO_3$—]+[$CO_3$—$^2$]) without oxidation, and measurement of total carbon (TC) concentration after oxidation. TOC is then computed from the difference (TOC=TC-IC). For samples containing high levels of inorganic carbon and lower levels of TOC, an IC removal module may be used to remove the inorganic carbon and permit accurate TOC measurements. A supply of the acid and oxidizer may be pre-packaged and stored in the analyzer, eliminating the need for reagent preparation by the analyst. Deionized water is continuously produced in the analyzer using a mixed-bed ion exchange resin with a capacity for several years of operation. The maintenance required is replacement of the reagent containers several times a year, replacement of the UV lamp and replacement of the pump tubing. The ease of use, low maintenance requirements and dependable performance has made this device the TOC analyzer of choice for monitoring water purification systems in semiconductor manufacturing, the pharmaceutical industry and conventional and nuclear power plants.

It is important that the amount of persulfate or other oxidizer added to the sample be sufficient to fully oxidize the sample. However, it is also important not to add excess oxidizer to the point that gas bubbles form in the sample. Gas bubbles are undesirable because the carbon dioxide dissolved in the sample will diffuse into the oxygen bubbles. If the oxygen bubble diffuses through the membrane and into the deionized water stream, the result will be a negative spike in the measured conductivity as the bubble passes through the conductivity cell due to the changed flow volume.

This has been addressed in the past by controlling the addition of oxidizer based on the expected approximate range of carbon concentration. For example, the oxidizer flow rate would be set relatively low if the expected carbon concentration were in the 1 to 5 ppm range, and the oxidizer flow rate would be set higher if the expected carbon concentration were in the 25 to 50 ppm range. This is a very effective approach. However, it would be desirable for the device to produce accurate readings across a broad range of carbon concentrations with a minimum of experimentation or prior knowledge about the approximate expected carbon concentrations.

It has also been found in utilizing prior devices that chloride in the sample tends to lead to inaccurate measurements of carbon concentrations, because the chloride preferentially interacts with hydroxyl radicals to the exclusion of organics, thus exhausting the oxidizer before the organics are fully oxidized.

SUMMARY OF THE INVENTION

In one embodiment of the present invention, an aqueous sample stream is passed through a filter to remove any particulate matter. Acid is added to produce a pH of less than 4. Inorganic carbon species—primarily carbonate and bicarbonate ions—are reacted with the acid to form carbon dioxide, while organic compounds remain unreacted. Also added is an oxidizer such as persulfate.

The sample is then split into a total carbon stream and an inorganic carbon stream. The total carbon stream is directed into an oxidation module. The oxidation module may utilize an oxidizing agent such as persulfate. The oxidation module may incorporate either direct U.V. oxidation using short wavelength U.V. radiation, semiconductor catalyzed U.V. oxidation using short wavelength U.V. radiation, or U V. oxidation in the presence of oxygen and or other oxidizing agents. The U.V. radiation may be generated particularly well using a narrow band excimer source. The oxidizing agents may be generated in-situ by the electrolysis of water and other chemical reagents such as sodium sulfate. In the oxidation module, organic compounds are converted to carbon dioxide.

The degree of oxidation potential in the oxidation module is not constant over time. Instead, the oxidation module operates in cycles in which the oxidation changes from near zero to a maximum gradually over a period of time such as three or four minutes. By gradually increasing, or "ramping," the oxidizer rate over a timed cycle, there is assurance that the optimum oxidizer rate is achieved at some point in the cycle.

The carbon dioxide formed in the photoreactor is sensitively measured using a carbon dioxide sensor. The sensor is comprised of a carbon dioxide selective gas permeable membrane which separates the acidified sample stream from a deionized water reservoir. The deionized water is continuously generated by means of a mixed bed ion exchange resin. Alternatively, deionized water can be supplied from a source external to the apparatus described in the present invention. The deionized water in one embodiment may be maintained at a positive pressure such as approximately 5–6 PSI higher than the sample stream pressure to inhibit bubble formation in the deionized water side.

As the carbon dioxide enters the deionized water, the carbon dioxide will dissolve in the water and cause an increase in the conductivity of the aqueous solution. The deionized water then flows into a conductivity cell in order to measure the increase in the concentration of ionic species. There is a deoxygenation module in the deionized water loop to remove oxygen gas from the water after it passes through the conductivity cell on its way to the next pass across the semipermeable membrane.

The increase in conductivity observed in the deionized water can be directly related to the concentration of carbon dioxide in the sample stream and hence the level of organic compounds originally present in the sample stream.

Simultaneous with the flow of the total carbon stream, the inorganic carbon stream flows through a delay tubing to compensate for the period of time the total carbon stream is in the oxidation reactor. The inorganic carbon stream then flows with its own separate carbon dioxide sensor which functions similarly to the carbon dioxide sensor for the total carbon stream. The device thus accurately measures both total carbon and inorganic carbon. Total organic carbon can be determined by subtracting the inorganic carbon measurement from the total carbon measurement.

DETAILED DESCRIPTION OF THE PREFERRED EMBODIMENT

The measurement of the total organic content of aqueous samples has become a standard technique for determining the quality of potable water, industrial process water and industrial and municipal waste waters.

The determination of the organic content of water samples is most commonly achieved by oxidation of the carbon constituents to carbon dioxide using chemical oxidizing agents, U.V. radiation, electrolysis, high temperature combustion, or a combination of these methods and subsequent detection of the carbon dioxide using IR spectroscopy or by conductometric or potentiometric techniques. The present invention is an improved process and apparatus for determining concentration levels of total organic and inorganic carbon compounds in aqueous samples.

Figure 1:
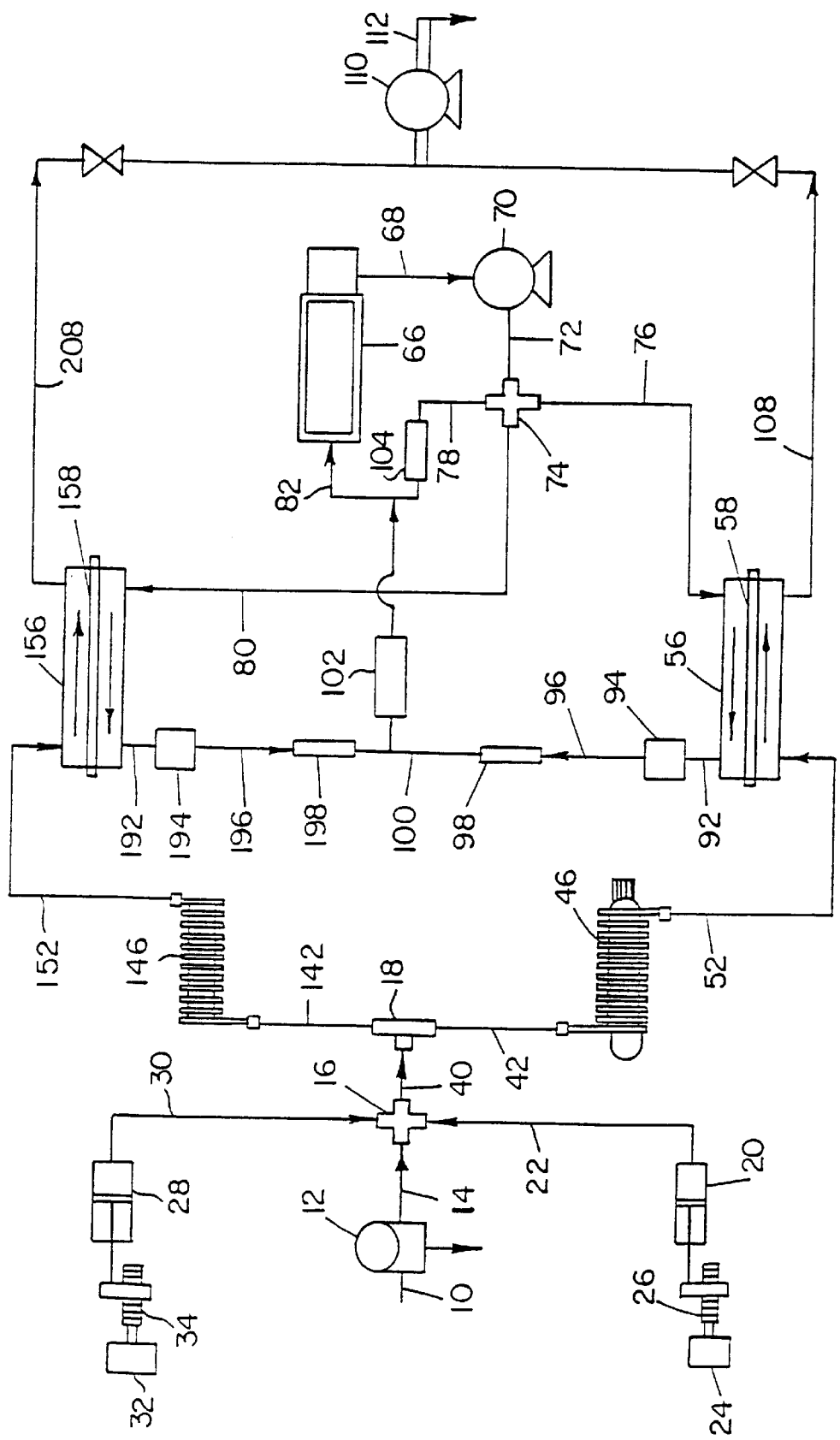
FIG. 1 is a block diagram depicting an embodiment of the present invention for the on-line measurement of carbon concentrations in accordance with the present invention.

A block diagram of one embodiment of the present invention is shown in FIG. 1. An aqueous sample inlet opening 10 is in communication with a particle filter 12 for the removal of particulate matter that may be suspended in the aqueous sample stream. A filter outlet conduit 14 joins a fitting 16. An acid reagent (6 M $H_3PO_4$ in the preferred embodiment) is delivered to the fitting 16 via a pump such as the acid syringe pump 20 shown in FIG. 1 through an acid line 22. The syringe pump 20 is driven by a motor 24 and worm gear 26 in the manner well known in the field of syringe pumps. An oxidizer reagent (15% $(NH_4)_2S_2O_8$) is delivered to the fitting 16 via another pump such as the oxidizer syringe pump 28 shown in FIG. 1 through an oxidizer line 30. The oxidizer syringe pump 28 is also driven by a motor 32 and worm gear 34 in the conventional manner.

The aqueous outlet conduit 40 from the fitting 16 is split into a conduit 142 for the measurement of inorganic carbon and a conduit 42 for the measurement of total carbon. It is noted that a vacuum degasser may be placed in or near the conduit 40 to remove gas from the sample stream which may interfere with the later carbon measurements. The conduit 42 leads to a U.V. oxidation reactor 46. Several U.V. oxidation reactors are described in detail in U.S. Pat. No. 5,132,094 by Godec, of which the present is a continuation-in-part and the contents of which are hereby incorporated by reference. Briefly, the aqueous sample inlet of the U.V. oxidation module is in communication with a coiled fused silica tube with an internal diameter of approximately 1 mm. The radius of the coil is such that a U.V. radiation source can be positioned in the annular region of the fused silica coiled tube. A suitable power supply and electrical connections (not shown) are used for the operation of the U.V. radiation source, which may consist of any known device which emits U.V. radiation, such as a gas discharge tube or mercury vapor discharge tube. An excimer lamp emitting light concentrated around 172 nm or other desired frequencies may be particularly useful. The design of the U.V. oxidation module has been demonstrated to provide high efficiency conversion of organic compounds to form carbon dioxide from aqueous samples at concentrations up to about 50 mg/L total organic carbon, with the addition of oxygen or other chemical oxidizing reagents such as persulfate.

The U.V. oxidation module outlet conduit 52 is in communication with the aqueous sample inlet of the total carbon, carbon dioxide sensor 56, which contains a carbon dioxide gas permeable membrane 58 positioned such that the flowing aqueous sample stream passes on one side of the carbon dioxide gas permeable membrane. On the other side of the membrane 58 passes deionized water. A thin layer of deionized water (approximately 0.01 inch) is maintained on the deionized water side of the gas permeable membrane to facilitate rapid analysis times.

The deionized water portion consists of a mixed bed 66 of anion and cation ion exchange resins in communication via a conduit 68 with a circulating pump 70 which is in communication via a conduit 72 to a joint 74. One outlet of the joint 74 is in communication via conduit 76 with the deionized water inlet of the total carbon, carbon dioxide sensor 56. Another outlet of the joint 74 in communication with the ion exchange resin bed 66 through conduit 78 and restrictor 104. The last outlet of the joint 74 is in communication via conduit 80 with the deionized water inlet of the inorganic carbon, carbon dioxide sensor 156 as described below.

The deionized water outlet of the total carbon, carbon dioxide sensor 56 is in communication via a conduit 92 to the inlet of a micro-conductivity and temperature sensor 94. The outlet of the micro-conductivity and temperature sensor 94 is in communication via a conduit 96 to a deoxygenation module 98.

The restrictor-deoxygenation module 98 is a length of gas-permeable tubing. Any gas in the deionized water tends to permeate through the tubing and out of the water. The tubing may also serve as a restrictor to maintain a pressure differential of 6–7 psi between the deionized water and the sample in modules 56 and 156. Therefore, gas that may tend to be in bubble form in the sample is more likely to remain dissolved in the deionized water stream. A pressure source may also be added to the deionized water stream to maintain this pressure differential, although the circulating pump 70 alone may be sufficient by properly sizing restrictor 104.

The aqueous sample outlet conduit 108 of the carbon dioxide sensor 56 is in communication with the inlet of a peristaltic sampling pump 110, and the outlet of the sampling pump is connected via a conduit 112 to a suitable waste container (not shown). The micro-conductivity and temperature sensor 94 is connected to a suitable power supply (not shown) and the electrical output from the micro-conductivity and temperature sensor is connected to a control and signal electronics module (not shown). The control and electronic module is comprised of a computer or other electronic device which is capable of controlling the voltages and currents to all of the electrical components of the present invention, actuation of valves and switches in a predetermined timed sequence, processing of the electrical signal from the micro-conductivity and temperature sensor, and the calculation of total organic carbon concentration, total carbon concentration and total inorganic carbon concentration from output of the micro-conductivity and temperature sensors.

The conduit 142 for the measurement of inorganic carbon leads to a coil of delay tubing 146. The purpose of the delay tubing 146 is to delay the sample flow for a period equal to the delay produced by the sample flowing through the U.V. oxidation reactor 46 on the total carbon side of the device. Therefore, the delay tubing 146 is simply a coil of inert tubing. The outlet of the delay tubing 146 is in communication with a conduit 152 leading to the inorganic carbon, carbon dioxide sensor 156. The inorganic carbon, carbon dioxide sensor 156 is similar to the total carbon, carbon dioxide sensor 56. A gas permeable membrane 158 is positioned such that the flowing aqueous sample stream passes on one side, and deionized water passes in the opposite direction on the other side. The deionized water is in a thin layer of approximately 0.01 inches to facilitate rapid analysis times. Upon leaving the inorganic carbon, carbon dioxide sensor 156 via conduit 208, the sample is drawn into sample pump 110 and discarded to a waste container via conduit 112.

The deionized water loop for the inorganic carbon side is similar to the deionized water loop for the total carbon side. It includes the same ion exchange resin bed 66, circulating pump 70, and joint 74. The last outlet 80 of the joint 74 is in communication with the deionized water inlet of the inorganic carbon dioxide sensor 156. From the inorganic carbon, carbon dioxide sensor 156, the deionized water flows through a conduit 192 and into an inorganic carbon micro-conductivity sensor 194. The deionized water then flows through a conduit 196, through a restrictor 198 or restrictor/deoxygenator, and joins the other deionized water loop in the oxygen degasser 102.

In the typical operation of the present invention as described in FIG. 1, the peristaltic sampling pump 110 withdraws an aqueous sample via the sample inlet opening 10, at a desired flow rate of 340 microliters per minute through the particulate filter 12. Aqueous acid, such as phosphoric acid or sulfuric acid, is introduced into the sample at the fitting 16 at a controlled rate of approximately 1 uL/min by the acid syringe pump 20. The desired pH of the aqueous sample after acidification is about 2.

The acidification of the sample stream will convert inorganic species to carbon dioxide, but will not convert organic species to carbon dioxide. The conversion of organic species to carbon dioxide requires the U.V. (or other type) oxidation module.

Also introduced at the fitting 16 in the preferred embodiment is an oxidizer such as persulfate as discussed above, via the oxidizer syringe pump 28 and oxidizer line 30. Rather than introducing oxidizer at a constant rate, however, oxidizer is introduced at rates that vary over an oxidizer rate cycle. At the start of a given oxidizer cycle, the oxidizer is introduced at a very low rate or at a zero rate. The rate gradually increases over the period of the cycle (210 seconds in the preferred embodiment) until reaching a maximum rate. The cycle then repeats.

The reason for the varying oxidizer rate is to ensure that the optimum oxidation is achieved at some point in the cycle to produce the highest carbon measurement downstream. If too little oxidizer is introduced, the carbon will be incompletely oxidized. In that event, insufficient carbon in the form of carbon dioxide will pass through the semipermeable membranes 58 and 158 in the carbon dioxide sensors 56 and 156 for downstream measurement in the conductivity cells 94 and 194. The result will be an inaccurately low carbon measurement. Conversely, if too much oxidizer is introduced, oxygen bubbles will form which will interrupt or lower the conductivity measurement in the micro-conductivity and temperature sensors 94 and 194, also resulting in an inaccurately low carbon measurement. Thus the accurate carbon measurement will be the one resulting from the highest conductivity measurement in the conductivity cells over the oxidizer rate cycle.

Figure 2:
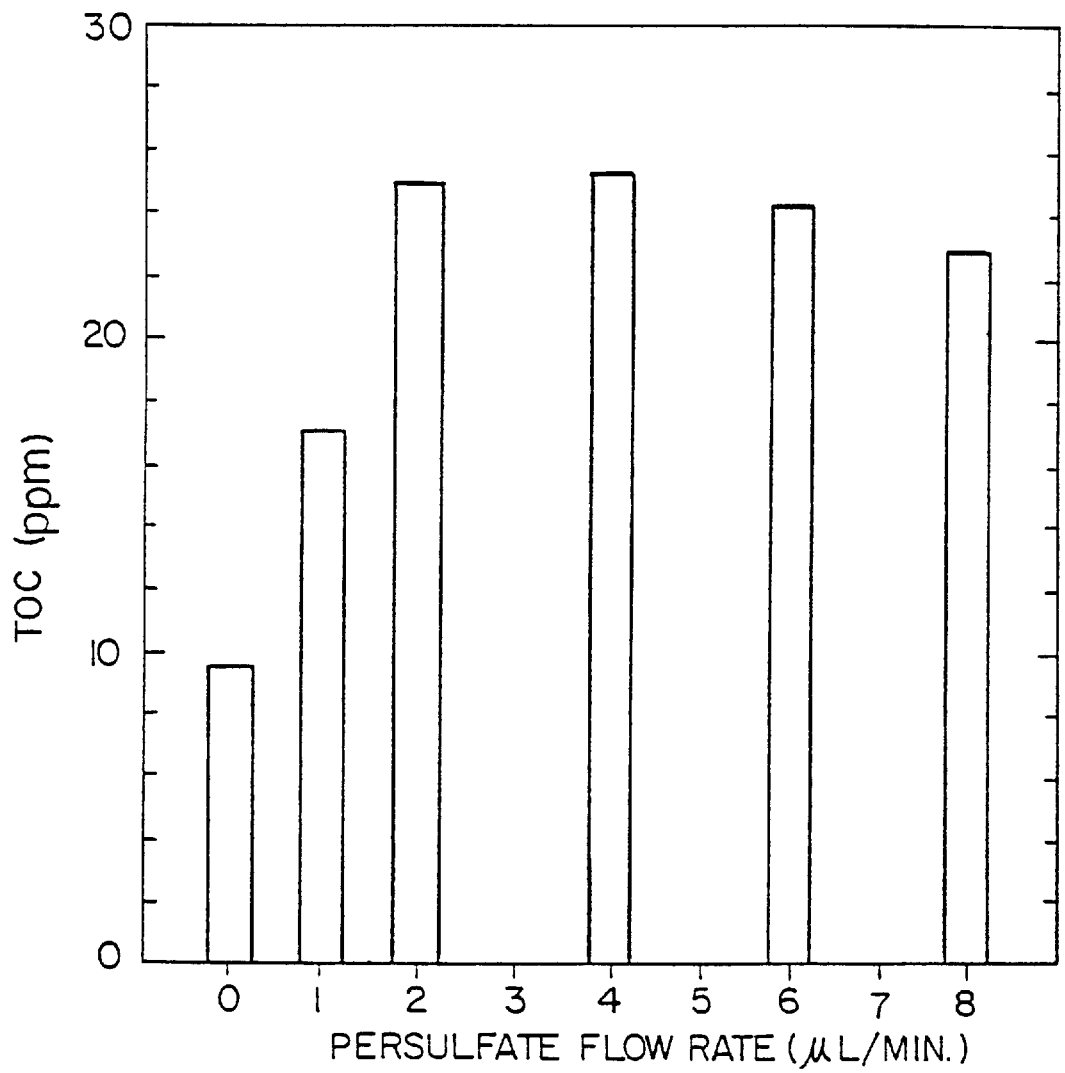
FIG. 2 is a representation of the output from the conductivity sensor and the flow rate of oxidizer over a measurement cycle.
Figure 3:
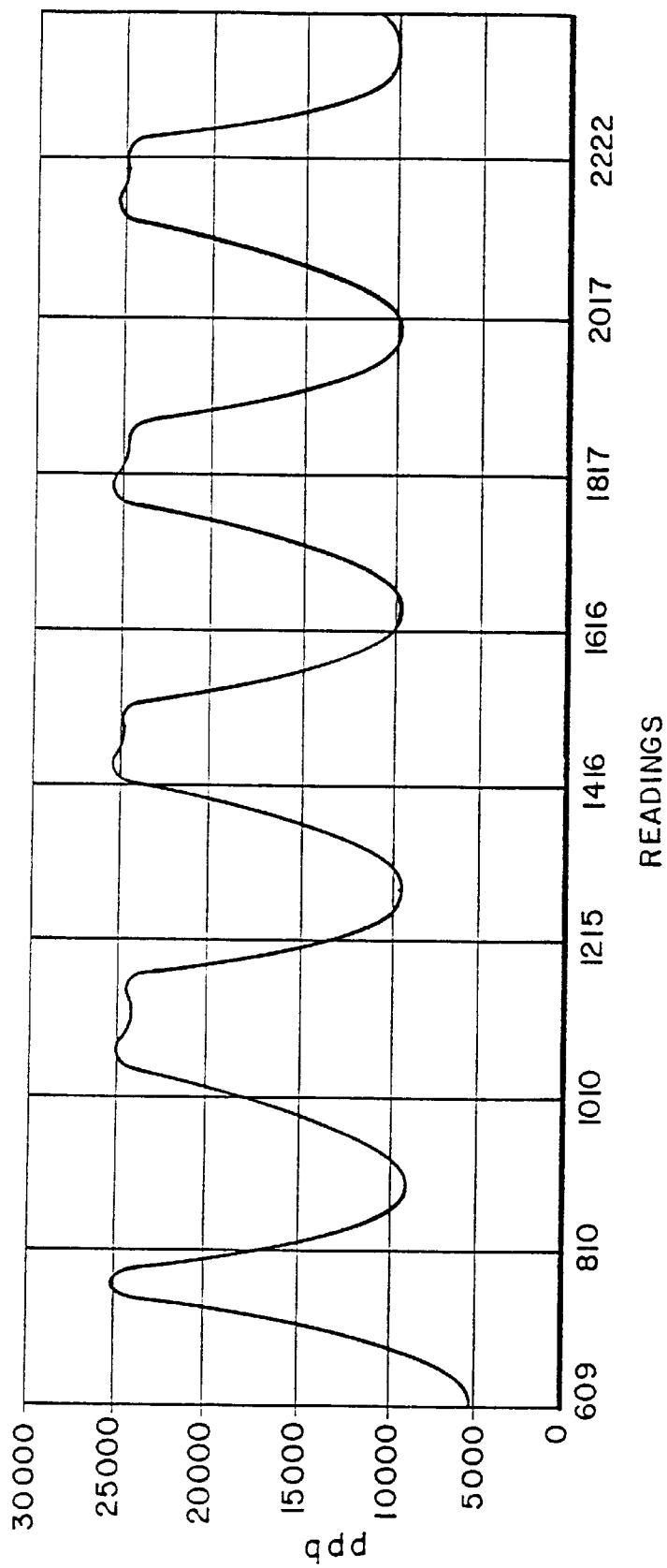
FIG. 3 is a graph of measured carbon versus time for a preferred embodiment of the invention.

In the depiction of FIG. 2, a 25 ppm KHP standard solution was analyzed using a persulfate oxidizer cycle varying from 0 to 6 uL/min. Because the U.V. light source in the oxidation reactor is on during the entire cycle, some oxidation takes place even when the oxidizer rate is 0, which is reflected in the carbon determination shown in FIG. 2 of almost 10 ppm at the 0 oxidizer rate. As the persulfate ramp is started, the measured TOC increases, reaching a maximum value at some point during the ramp. As the ramp is continued, excess persulfate is added, leading to the formation of oxygen bubbles in the sample stream and a depression in the measured TOC. When the persulfate flow rate is stopped, the measured TOC decreases back to the U.V. light only value. As the next persulfate ramp is started, the cycle is repeated, with the measured TOC increased to a maximum value then decreasing as excess persulfate is added. The maximum TOC value obtained during a ramp is used to calculate the TOC of the sample stream.

The embodiment described in the preceding paragraphs contemplates an oxidizer rate that starts at a minimum and gradually increases to a maximum over the oxidizer cycle. However, it will be apparent that the invention could as easily utilize some other oxidizer rate profile such as a profile in which the rate starts at a maximum and gradually declines to a minimum or the rate varies in some other fashion. The important concept is that the oxidizer rate does vary within a predetermined range, to ensure that it is at the optimum range at some point in the cycle.

The aqueous sample stream is split at fitting 18 into the total carbon stream and the inorganic carbon stream. The total carbon stream enters the U.V. oxidation reactor 46 where organic compounds are converted to carbon dioxide and other products. Simultaneously, the inorganic stream enters the delay tubing 146. The two streams then enter their respective carbon dioxide sensors 56 and 156 simultaneously; that is, the portion of the sample entering the total carbon, carbon dioxide sensor 56 at a given moment was separated from the portion of the sample entering the inorganic carbon, carbon dioxide sensor 156 at that same moment.

The aqueous sample stream effluent of the U.V. oxidation reactor 46 is directed via conduit 52 into the aqueous sample inlet of the total carbon, carbon dioxide sensor 56, out through the aqueous sample outlet of the total carbon, carbon dioxide sensor 56 through the peristaltic sample pump 110 to a suitable waste container. Similarly, the aqueous sample stream effluent of the delay tubing 146 is directed via conduit 152 into the aqueous sample inlet of the inorganic carbon, carbon dioxide sensor 156, out through the aqueous sample outlet of the inorganic carbon, carbon dioxide sensor 156 through the peristaltic sample pump 110 to the waste container. Temperature measurements are also taken at or proximate the conductivity cells 94 and 194 so that the carbon determinations can take into consideration the sample temperatures.

A continuous supply of deionized water is produced in the deionized water portion by passing an aqueous stream of water through the mixed bed ion exchange resins 66 by means of the circulating pump 70. The deionized water flows in two loops: one is the total carbon loop and the other is the inorganic carbon loop. In the total carbon loop, deionized water flows from fitting 74 via conduit 76 into the deionized water inlet of the total carbon, carbon dioxide sensor 56. As the sample stream passes on one side of the gas permeable membrane 58 of the total carbon, carbon dioxide sensor 56, the carbon dioxide formed upstream will diffuse across the gas permeable membrane 58 into the deionized water sample on the opposite side of the membrane, where the carbon dioxide will be converted into ionic species. In the inorganic carbon, carbon dioxide loop, deionized water flows from fitting 74 via conduit 80 into the deionized water inlet of the inorganic carbon, carbon dioxide sensor 156. As the sample stream passes on one side of the gas permeable membrane 158 of the inorganic carbon, carbon dioxide sensor 156, the carbon dioxide formed upstream by conversion of the inorganic carbon to carbon dioxide in the acification step will diffuse across the gas permeable membrane 158 into the deionized water sample on the opposite side of the membrane, where the carbon dioxide will be converted into ionic species. The increase in conductivity caused by the presence of ionic species formed from carbon dioxide is measured by the micro-conductivity and temperature cells 94 and 194. The observed increase in the conductivity of the deionized water sample can be directly related to the concentration of carbon dioxide present in the aqueous sample streams, and hence, the level of total carbon and inorganic carbon compounds present in the aqueous sample stream.

The carbon dioxide membrane 58 or 158 employed in the carbon dioxide sensors in one embodiment of the present invention may advantageously be constructed from a Teflon-like material, perfluoroalkoxy resin ("PFA"). As shown in Table I, the use of this material in the carbon dioxide sensor provides significantly higher selectivity for the passage of carbon dioxide compared with other compounds which may be present in aqueous samples and potentially interfere in the measurement of carbon dioxide using the conductomeric technique described in U.S. Pat. Nos. 5,132,094 and 5,443,991. For comparison purposes, data reported by Kobos et al. in 54 Anal. Chem. 1976–1980 (1982) are included in Table 1.

TABLE 1

Selectivity of permeable membranes:
potential interferences in CO₂ measurements

| Compound | Spike Concentration | PFA | Porous PTFE | Tefzel |
|---|---|---|---|---|
| I₂ | 13 ppm | ND | — | — |
| HNO₃ | 1000 ppm | ND | — | — |
| Na₂SO₄ | 1000 ppm | ND | — | — |
| Na₂SO₃ | 21 ppm | ND | 1 | 0.4 |
| NaNO₂ | 11 ppm | 0.2 | 5 | 0.6 |
| NaCl | 1000 ppm | ND | — | — |
| NaOCl | 10 ppm | ND | — | — |
| Na₂S | 15 ppm | 0.05 | 6 | 0.4 |
| Na₂S | 150 ppm | 2.0 | 30 | 2.0 |
| Formic Acid | 10 ppm | ND | 1 | 0.7 |
| Acetic Acid | 10 ppm | ND | 1 | 0.6 |

From Kobos et al.
ND: no detectable increase
—: data not reported

The measurements at the micro-conductivity and temperature sensors 94 and 194 can take place virtually continuously or at periodic intervals such as those shown in FIG. 2 over the course of an oxidation rate cycle. Once a cycle is completed, the highest measured carbon is deemed the correct measurement, and the other measurements are deemed flawed due to insufficient oxidation or overoxidation resulting in bubble formation. Thus a single correct measurement is obtained for each cycle. Sequential correct measurements are obtained in sequential periods, each period corresponding to the cycle length. Thus a device utilizing 210 second cycles can obtain a correct measurement approximately every 210 seconds.

After the deionized water streams leave the micro-conductivity and temperature sensors 94 and 194, they pass through the deoxygenation modules 98 and 198 which maintain a pressure differential. The two deionized water samples then join and flow into the exchange resin bed 66 via the conduit 82, then to the pump 70, and back to the splitting fitting 74 to complete the cycle. The deionized water continuously circulates through the exchange resin bed 66. Only a small fraction of that circulation is tapped for circulation through the total carbon loop and inorganic carbon loop.

It can be appreciated that the device and method of the present invention can be used to make one or more of several determinations. Total carbon can be determined by the total carbon, carbon dioxide sensor. Inorganic carbon can be determined by the inorganic carbon, carbon dioxide sensor. Finally, organic carbon can be determined by subtracting the inorganic carbon determination from the total carbon determination.

The present invention represents a significant improvement over the methods and apparatus existing for the measurement of total organic carbon, total inorganic carbon, and total carbon content of aqueous samples. The present invention can be used for these determinations in a wide range of samples, with minimal use of external chemical reagents, and without prior knowledge of the approximate carbon range in the sample. The use of a carbon dioxide selective membrane and conductometric detection applied to the measurement of total organic carbon and total inorganic carbon concentrations in aqueous samples offers several advantages: 1) no purge gas, gas/liquid purge apparatus or drying system is required, 2) the conductometric detection system provides excellent long-term calibration stability (over one year between calibrations) and minimal fouling or contamination since the sensor is only exposed to carbon dioxide in deionized water, 3) the size of the conductivity sensor can be sufficiently small that accurate measurement in samples as small as 0.1 mL can be achieved, 4) conductometric detection provides a large linear dynamic range, typically one to three orders of magnitude greater than other techniques utilized for the measurement of carbon dioxide in aqueous samples, 5) the sensitivity of the carbon dioxide sensor and conductivity detector is substantially better than in other techniques, 6) no sample clean-up or dilution is required, and 7) the combination of an inorganic carbon removal module and a carbon dioxide sensor virtually eliminates any interference from other volatile gases.

What is claimed is:

1. A process for determining carbon concentration in an aqueous sample, said process comprising the steps of:
   (a) flowing a fluid including at least said aqueous sample at a controlled flow rate;
   (b) reacting carbon in said aqueous sample to produce organic carbon oxidation products by providing and varying oxidizing conditions in said fluid which are varied in a controlled and reproducible manner during a predetermined oxidation period over a range comprising at least two oxidation potentials so as to generate a profile of differing concentrations of organic carbon oxidation products in said fluid corresponding to the different oxidation potentials;
   (c) measuring the concentration of organic carbon oxidation products in said fluid at said at least two oxidation potentials; and,
   (d) determining the carbon concentration in said aqueous sample from the measures of organic carbon oxidation products in said fluid at said at least two oxidation potentials.

2. A process according to claim 1 wherein said oxidizing conditions in said fluid are varied in a controlled and reproducible manner using at least one process selected from the group comprising:
   (a) varying the flow rate of said fluid;
   (b) varying the rate of addition of an oxidizer to said fluid;
   (c) varying the flow rate of said fluid past a location where the fluid is exposed to ultraviolet light;
   (d) flowing said fluid past a location where the aqueous sample is exposed to ultraviolet light while varying the intensity of the ultraviolet light; and
   (e) varying the rate of generation of an oxidizer in an apparatus which is in fluid communication with said fluid.

3. A process according to claim 1 wherein at least one of said at least two oxidation potentials in said fluid is selected from the following
   (a) an oxidation potential that is sufficient to substantially completely react the organic carbon in said aqueous sample;
   (b) an oxidation potential greater than that necessary to substantially completely react the organic carbon in said aqueous sample;
   (c) an oxidation potential that is above oxygen saturation conditions for said fluid; and,
   (d) an oxidation potential that is maintained at a substantially constant level for a controlled period of time.

4. A process according to claim 1 wherein the oxidizing conditions in said fluid are smoothly and continuously varied from a first oxidation potential to a second oxidation potential, one of said first and second oxidation potentials being below that which is necessary to substantially completely react all of the carbon in said aqueous sample, the other of said first and second oxidation potentials being above that which is necessary to substantially completely react all of the carbon in said aqueous sample.

5. A process according to claim 1 wherein the concentration of carbon dioxide in said organic carbon oxidation products in said aqueous sample is measured utilizing a carbon dioxide gas permeable membrane and further comprising the step of flowing said fluid on one side of the membrane which separates said fluid from contact with a second fluid.

6. A process according to claim 2 wherein at least one of said at least two oxidation potentials in said fluid is selected from the following:

(a) an oxidation potential that is sufficient to substantially completely react the organic carbon in said aqueous sample;

(b) an oxidation potential greater than that necessary to substantially completely react the organic carbon in said aqueous sample;

(c) an oxidation potential that is above oxygen saturation conditions for said fluid; and, (d) an oxidation potential that is maintained at a substantially constant level for a controlled period of time.

7. A process according to claim 1 wherein the oxidizing conditions provided in said fluid are varied from a first oxidation potential to at least a second, higher oxidation potential.

8. A process according to claim 1 wherein the oxidizing conditions provided in said fluid are varied from a first oxidation potential to at least a second, lower oxidation potential.

9. A process according to claim 1 wherein providing oxidizing conditions in said fluid includes the step of establishing and maintaining each of said at least two oxidation potentials at a substantially constant level for a controlled period of time.

10. A process according to claim 9 wherein said at least two oxidation potentials are maintained at constant levels for substantially equal periods of time.

11. A process according to claim 9 wherein said at least two oxidation potentials are maintained at constant levels for differing periods of time.

12. A process according to claim 1 wherein providing oxidizing conditions in said fluid includes the step of smoothly and continuously varying the oxidation potential from a level below that necessary to substantially completely react all of the organic carbon in the aqueous sample to carbon dioxide to an oxidation potential level above that necessary to substantially completely react all of the organic carbon in the aqueous sample to carbon dioxide.

13. A process according to claim 1 wherein providing oxidizing conditions in said fluid includes the step of smoothly and continuously varying the oxidation potential from a level above that sufficient to substantially completely react all of the organic carbon in the aqueous sample to carbon dioxide to an oxidation potential level below that sufficient to substantially completely react all of the organic carbon in the aqueous sample to carbon dioxide.

14. A process according to claim 1 wherein said oxidizing conditions in said fluid are varied in a controlled and reproducible manner by varying the rate of generation of one or more oxidizers in an electrolysis cell which is in association with said fluid.

15. A process according to claim 14 further including the steps of removing at least some hydrogen from said fluid.

16. A process according to claim 1 wherein said oxidizing conditions in said fluid are varied in a controlled and reproducible manner by flowing said fluid containing at least sufficient oxidizer for substantially complete reaction of organic compounds in said aqueous sample to carbon dioxide, past a location where the aqueous sample is exposed to ultraviolet light while varying the exposure of the sample to ultraviolet light.

17. A process according to claim 16 wherein said aqueous fluid contains sufficient dissolved oxygen relative to the content of organic carbon in said sample for substantially complete reaction of organic compounds to carbon dioxide.

18. A process according to claim 16 wherein exposure of the sample to ultraviolet light is varied by varying the intensity of ultraviolet light.

19. A process according to claim 16 wherein exposure of the sample to ultraviolet light is varied by varying the duration of the exposure.

20. A process according to claim 16 wherein exposure of the sample to ultraviolet light is varied by varying the flow rate of the sample past the ultraviolet light.

21. A process according to claim 16 further including the step of adding an oxidizer to said fluid.

22. A process according to claim 21 wherein said oxidizer is an electrolyte.

23. A process according to claim 21 wherein said oxidizer comprises at least a persulfate.

24. A process according to claim 21 wherein said oxidizer is a non-electrolyte.

25. A process according to claim 21 wherein the step of adding an oxidizer to said fluid includes generating an oxidizer in an ectrolysis cell which is in association with said fluid.

26. A process according to claim 25 further including the step of removing at least some hydrogen from said fluid.

27. A process according to claim 1 wherein step of measuring organic carbon oxidation products in said fluid includes flowing said fluid into contact with one side of a first $CO_2$-permeable membrane, the opposite side of which is in contact with a second fluid.

28. A process according to claim 27 wherein said first $CO_2$-permeable membrane is a $CO_2$-selective membrane.

29. A process according to claim 28 wherein said $CO_2$-selective membrane consists essentially of perfluoroalkoxy resin.

30. A process according to claim 27 further including the step of sensing changes in the carbon dioxide content of said second fluid.

31. A process according to claim 27 further including the step of sensing changes in temperature of conductivity of said second fluid.

32. A process according to claim 27 wherein said second fluid is deionized water.

33. A process according to claim 1 further including the step of determining the inorganic carbon content of said aqueous sample.

34. A process according to claim 33 wherein said step of determining the inorganic carbon content includes converting inorganic carbon in said aqueous sample to carbon dioxide.

35. A process according to claim 34 further including the step of measuring the concentration of carbon dioxide in said fluid downstream from said converting step.

36. A process according to claim 35 wherein said step of measuring the concentration of carbon dioxide in said fluid downstream from said converting step includes flowing said fluid into contact with one side of $CO_2$-permeable membrane, the opposite side of which is in contact with a second fluid.

37. A process according to claim 36 further including the step of sensing changes in the carbon dioxide content of said second fluid.

38. A process according to claim 36 wherein said $CO_2$-permeable membrane is a $CO_2$-selective membrane.

39. A process according to claim 38 wherein said $CO_2$-selective membrane consists esseally of perfluoralkoxy resin.

40. A process according to claim 36 further including the step of sensing changes in temperature or conductivity of said second fluid.

41. A process according to claim 36 wherein said fluid is deionized water.

42. A process according to claim 16 wherein said ultraviolet light is generated by gas discharge tubes, mercury vapor discharge tubes, or excimer lamps.

43. A process for determining the carbon content of each of a series of water samples containing organic compounds comprising the following steps:
 (a) introducing one of said water samples into a first fluid flow path and moving said sample from an upstream location along said flow path at a controlled flow rate to a downstream location along said flow path;
 (b) passing said sample through a first reaction zone along said flow path, said first reaction zone being between said upstream and downstream locations, and exposing different portions of said sample to controllable, differing oxidizing conditions at said first reaction zone, said oxidizing conditions for each sample passing through said first reaction zone including at least a first reproducible oxidizing condition which is insufficient to oxidize substantially all of the organic compounds in the sample to carbon dioxide and at least a second reproducible oxidizing condition which is sufficient to oxidize substantially all of the organic compounds in the sample to carbon dioxide;
 (c) sensing the carbon dioxide content of the different portions of said sample at a first sensing zone along said flow path downstream from said first reaction zone; and,
 (d) repeating steps (a) to (c) for subsequent water samples in the series utilizing substantially identical first and second oxidizing conditions.

44. A process according to claim 43 wherein said oxidizing conditions at said first reaction zone are varied in a controlled and reproducible manner using at least one process selected from the group comprising:
 (a) varying the flow rate of said sample;
 (b) varying the rate of addition of an oxidizer to said sample;
 (c) varying the flow rate of said sample through said first reaction zone where the sample is exposed to ultraviolet light;
 (d) flowing said sample through said first reaction zone where the sample is exposed to ultraviolet light while varying the intensity of the ultraviolet light; and,
 (e) varying the rate of generation of an oxidizer in an apparatus which is in fluid communication with said sample.

45. A process according to claim 43 wherein at least one said oxidation conditions at said first reaction zone is selected from the following:
 (a) an oxidizing condition that is above oxygen saturation conditions for said sample;
 (b) an oxidizing condition that is maintained at a substantially constant level for a controlled period of time;
 (c) an oxidizing condition that is established by applying electrolysis to said sample while it is passing through said first reaction zone; and,
 (d) an oxidizing condition that is established by applying electrolysis and ultraviolet light to said sample while it is passing through said first reaction zone.

* * * * *